United States Patent [19]

Grain

[11] Patent Number: 4,484,172

[45] Date of Patent: Nov. 20, 1984

[54] HUMIDITY SENSOR, COMPRISED OF COMPOUND METAL OXIDES WITH PEROVSKITE STRUCTURE

[75] Inventor: Clark F. Grain, Framingham, Mass.

[73] Assignee: Arthur D. Little, Inc., Cambridge, Mass.

[21] Appl. No.: 481,219

[22] Filed: Apr. 1, 1983

[51] Int. Cl.$^3$ .................................... H01L 7/00
[52] U.S. Cl. ................................ 338/35; 252/518
[58] Field of Search ............... 338/35, 34; 73/335, 73/336, 336.5; 252/521, 520, 519, 518; 422/98, 94

[56] References Cited

U.S. PATENT DOCUMENTS

| | | | |
|---|---|---|---|
| 3,922,204 | 11/1975 | Tseung et al. | 204/425 |
| 3,951,603 | 4/1976 | Obayashi et al. | 338/34 X |
| 4,015,230 | 3/1977 | Nitta et al. | 252/518 |
| 4,357,426 | 11/1982 | Murata et al. | 252/521 |

FOREIGN PATENT DOCUMENTS

| | | | |
|---|---|---|---|
| 17502 | 10/1980 | European Pat. Off. | 338/34 |
| 55104 | 6/1982 | European Pat. Off. | 422/94 |

*Primary Examiner*—C. L. Albritton
*Assistant Examiner*—C. N. Sears
*Attorney, Agent, or Firm*—Richard J. Hammond

[57] ABSTRACT

An improved humidity sensitive semiconductor device comprising an insulating base member and a humidity sensitive coating on said base member having at least two spread apart metal electrodes connected thereto, the coating comprising a metal oxide of a lanthanide cobaltate of the formula $L_{1-x}Sr_xCoO_3$ where L is a member of the lanthanide series of elements selected from the group lanthanum, cerium, praseodymium, neodymium, promethium, smarium, europium, gadolinium, terbium, sysprosium, holmium, erbium, thulium, ytterbium, and lutetium and x is from about 0 to about 0.5 and an anion selected from the group consisting essentially of the organic anions of monobasic acids, dibasic acids or polybasic acids, inorganic anions and mixtures thereof.

5 Claims, 6 Drawing Figures

HUMIDITY SENSOR, COMPRISED OF COMPOUND METAL OXIDES WITH PEROVSKITE STRUCTURE

BACKGROUND OF THE INVENTION

The present invention relates in general to humidity sensors or hygrometers and, more particularly, it relates to devices having electrical semi-conductivity which is a function of relative humidity. Still more particularly, this invention relates to humidity sensors of the type disclosed herein employing a lanthanide cobaltate.

DESCRIPTION OF THE PRIOR ART

In the prior art it has been recognized that the electrical resistance of certain metal oxides varies with changes in the relative humidity of the environment to which the oxide composition is exposed. The term "relative humidity" as commonly defined and used herein refers to the ratio of the quantity of water vapor actually present in the air to that amount which would saturate the air at the same temperature. It has also been recognized that relative humidity sensors could be fabricated utilizing the principle of changing electrical resistance with changing relative humidity inherent in these metal oxide materials. Of these, the most successful relative humidity sensors have been fabricated utilizing a metal oxide selected from the group including the oxides of the metals found in Group VIII, Period 4 of the Periodic Table.

Such detectors have two important disadvantages; their sensitivity is low and varies with the time.

An improved humidity detector the operation of which is based on a principle completely different from that of these conventional detectors is described in French Patent Specification No. 2,160,095 according to which the detector comprises a semiconductor substrate which consists of silicon, germanium or gallium arsenide and a major surface of which is partly covered with a layer of stannic oxide ($SnO_2$). The remainder of the surface is covered with a layer of silica ($SiO_2$) which serves to stabilize the characteristic of the semiconductor. Metal electrodes are applied to both major surfaces of the substrate, one on the stannic oxide layer and the other on the semiconductor surface.

It is disclosed that the device is in effect a Schottky junction which is particularly sensitive to variations in the ambient humidity.

Such a device is a considerable improvement on prior devices, but has serious disadvantages; its response is slow (15 seconds elapse before a response is obtained to a change in relative humidity from 100% to about 0%) and the slope of the characteristic of the Schottky diode as a function of relative humidity is steep, giving rise to detection and measurement inaccuracies. These inaccuracies are increased by the small area of contact of the sensitive region of the diode with the ambient atmosphere. Furthermore, the device consumes copious amounts of energy when measuring low humidities, with consequent undesirable heating of the device to temperatures higher than the ambient temperature.

In a recent patent U.S. Pat. No. 4,025,892, a probe is disclosed for selectively detecting polar molecules in a gaseous mixture, the operation of the probe being based on the variation of its electrical resistance due to a reaction at the probe surface. While the probe is effective at low levels of humidity, its non-linear response at higher levels are disadvantageous.

This invention obviates the aforementioned disadvantages of the known detectors.

It is an object of the present invention to provide an improved humidity sensor that is easier to fabricate than prior art devices.

It is a further object of the present invention to provide an improved humidity sensor of a lanthanide cobaltate.

It is still a further object of the present invention to provide an improved humidity sensor whose electrical resistance decreases as the water content in the air increases.

It is a further object of the present invention to provide an improved humidity sensor whose response to changes in humidity is rapid.

It is another object of the present invention to provide an improved humidity sensor that is very stable during periods of high humidity.

Various other objects and advantages of the invention will become clear from the following description of embodiments thereof, in conjunction with the accompanying drawings in which FIG. 1 is a perspective view of an embodiment of the humidity sensitive resistor device in accordance with the present invention;

Figure 5:
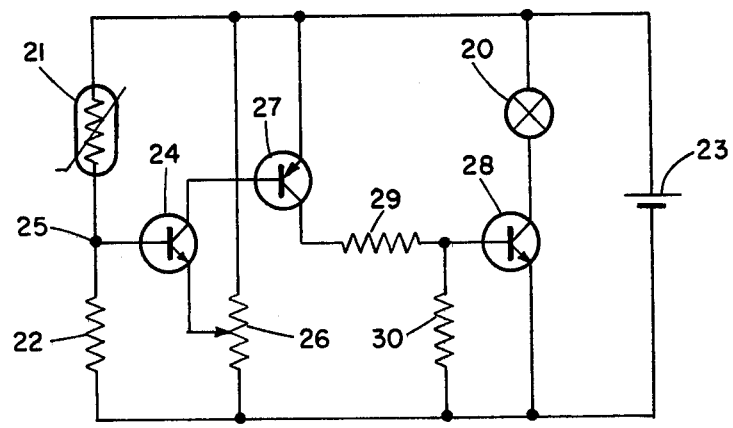

FIG. 5 schematic representation of an amplifier circuit for use with the humidity sensor in accordance with the present invention.

DESCRIPTION OF THE PREFERRED EMBODIMENTS

Referring now to the drawings in more detail, in FIGS. 1, 2A, 2B and 4, there are shown in perspective view, the basic structural features of the humidity sensitive semiconductor device according to one embodiment of the present invention. The humidity sensitive semiconductor device shown, basically comprises an insulating base member 10 having at least two spaced apart metal electrodes 11 and 12 connected to a humidity sensitive coating 13. The insulating base member may be made of any material that is a highly insulating dielectric such as illustrated by glass, quartz, the various ceramics, polystyrene or similar polymeric materials that can form solid insulating bases when used alone or applied over electrically conductive bases (such as metals). The base member should be clean, preferably chemically using detergents, water and organic solvents, the latter being applied by dipping or vapor degreasing.

The humidity sensitive coating is a metal oxide, such comprising a compound of the formula $L_{1-x}Sr_xCoO_3$ where L is a member of the lanthanide series of elements selected from the group lanthanum, cerium, prasedymium, neodymium, promethium, samarium, europium, gadolinium, terbium, dysprosium, holmium, erbium, thulium, ytterbium, and lutetium and x is from about 0 to about 0.5. Preferably L is cerium, erbium, gadolinium, lanthanium, neodymium, praseodymium, samarium, and ytterbium. Particularly preferred is when L is lanthanium. The metal oxide layer formed of the compound of the formula $L_{1-x}Sr_xCoO_3$ where L and x are herein defined has semiconductor conductivity of the p-type i.e., it is electron accepting. As such, the oxide has very high electrical resistance. As the amount of strontium increases however, the resistance of this composite decreases and, when the ratio of L to Sr becomes greater than 1:1, i.e., when $X > 0.5$ the semiconductor character of this layer is sufficiently impaired so as to undesirably diminish the humidity detection capability of the device (it becomes a conductor of electricity). The variation in the ability to pass the applied electrical current is, of course, a function of the water vapor content of the atmosphere to which the device is exposed, the greater such content, the more facile the conductivity. The sensitivity of the device is however related to the active humidity detection area. This area is the area exposed to contact with the humid atmosphere. Thus, the embodiment of FIGS. 1, 2A, and 4 while structurally quite different, could have identical sensitivity if the area of these sensors is identical.

In addition to the actual area of the oxide layer in those structures shown in the Figures, consideration must be given to the thickness of such layer since response time and sensitivity are both a function of the thickness of this layer. For detectors of relative rapid response, but somewhat decreased sensitivity, the layer should preferably be no greater than 50 microns, but may be as little as 10 microns. Greater sensitivity is obtained at thickness in excess of 50 microns. Layers in excess of 500 microns do not provide any further enhancement in sensitivity.

The semiconductor device according to the present invention is prepared by depositing the metal oxide layer on the insulating base member. For example, there may be adopted a method in which a powder of the metal oxide is formed into a paste and the paste is coated and dried on the insulating substrate to form a layer of metal oxide thereon. Furthermore, there may be adopted a method in which a thin film of metal is formed on the insulating substrate by vacuum deposition or the like and the metallic film is oxidized to form the metal oxide. Still further, there may be adopted a method in which powder of metal oxide is solidified by a press to form a block of metal oxide. Moreover, there may be adopted a method in which a salt of metal oxide is solidified on the substrate. In short, any method of deposition of the metal oxide is included in the scope of the present invention.

In order to facilitate connection of the oxide with external lead wires, electrodes of a noble metal such as gold are formed on the moisture responsive material. In such case, the layer of metal oxide formed on the insulating substrate can be prepared, for example, by taking a powder of the metal oxide and forming it into a paste. The paste is coated and dried on an insulating plate to form the film.

Preferably, the metal oxide is applied to the insulating substrate in the form of its water-soluble component salts, i.e., the correct atomic ratios of the water soluble salts of lanthanide, strontium and cobalt. After air drying, the solid mixture is placed in an oven at a temperature in which the salts decompose and interact to form the metal oxide layer of the formula $L_{1-x}SrCoO_3$ where L and x are as previously defined. Such temperature is typically at least about 200° C. up to about 400° C. Temperatures in excess of this disadvantageously affect the sensitivity of the resulting detector. After cooling, the metal oxide layer is ready for use.

In the preparation of the detector, it has been found advantageous to have incorporated in the metal oxide small amounts (from about 0.05–5%) of an anion. As such, organic anions such as those from the monobasic acids, e.g., acetic, propionic, buteric, benzoic, etc. the dibasic acids, e.g., oxalic, malonic, succinic, etc. or polybasic acids, e.g., ethylene tetracetic acid are of use for such incorporation. Similarly, the inorganic anions such as those of the halides, e.g., chloride, bromide, etc., sulfate, phosphates, arsenates, etc. can be used.

The preferred methods of preparation consist of coating a dielectric substrate with solutions of the salts of the metal ions of interest. These are then decomposed to the oxides. Preferred salts include the nitrates and chlorides.

EXAMPLE 1

A solution is prepared containing 4.20 grams of La(NO$_3$)$_2$.6H$_2$O, 2.91 grams of Co(NO$_3$)$_2$.4H$_2$O and 0.15 grams of Sr(NO$_3$)$_3$ dissolved in 150 cc of methanol. This solution is then dip coated onto the porous side of several alumina substrates and allowed to dry. The dried coatings and substrates are then heated to 175° C. for 30 minutes.

EXAMPLE 2

The same relative amounts of starting material as shown in Example 1 dissolved in water instead of methanol. The aqueous solution is diluted by a factor of ten and then sprayed onto heated glass or aluminum substrates, held at a temperature of 225° C. for 5 minutes.

EXAMPLE 3

An aqueous solution is prepared containing twice the amount of salts shown in Example 1 dissolved in 100 cc of water. An amount of hydrochloric acid sufficient to convert the nitrate salts to chlorides is added. This solution is spin coated onto an alumina substrate and allowed to dry. The dried coating and substrate are then heated, in air, to a temperatures of 325° C. for a period of 10 minutes.

Figure 3:
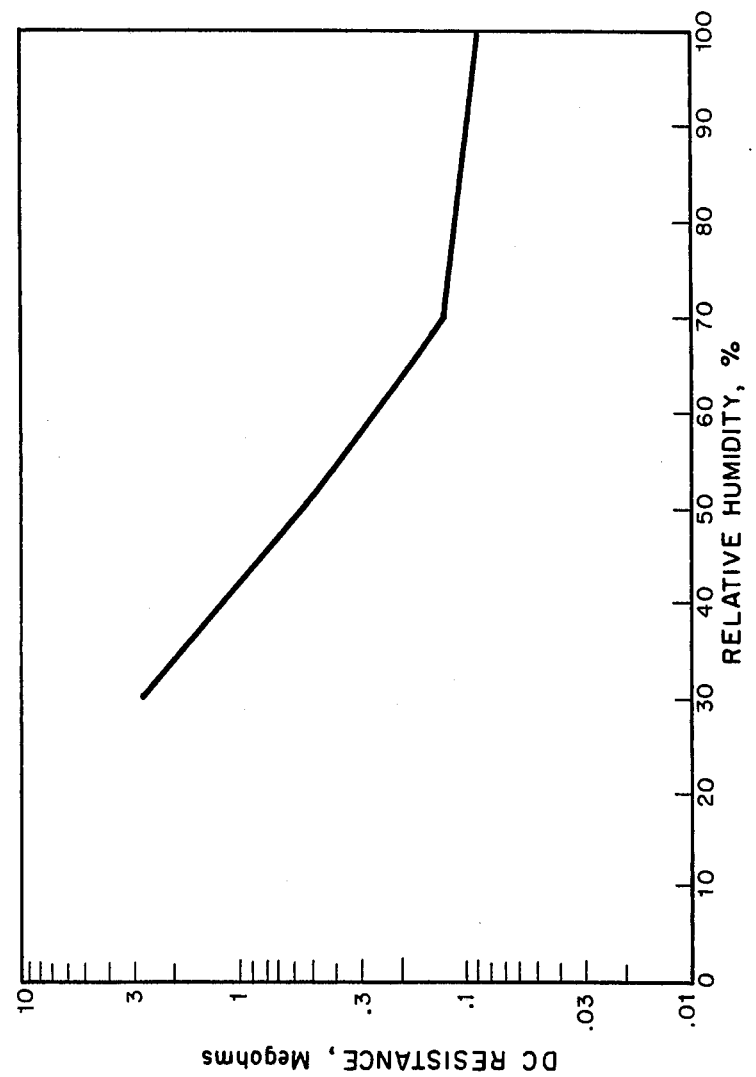
FIG. 3 is the response curve of the humidity detector of the present invention.

FIG. 3 is illustrative of typical response characteristics of the humidity detection of the present invention. As shown, response to changes in humidity is particularly good for low relative humidities, i.e., resistance of 2.5MΩ at RH of 30%.

The following Tables disclose the effect of various physical parameters on humidity sensors prepared in accordance with Example 1. Alumina substrate in all cases (Tables I-IV) All compositions the same, i.e., $La_{0.93}Sr_{0.07}CoO_3$.

TABLE I

| Relative Humidity (%) | Coating Thickness | | |
|---|---|---|---|
| | 40 | 200 | 600 |
| | Resistance, MΩ | | |
| 31 | 10$^3$ | 404 | 113 |
| 52 | 18 | 32 | 37 |
| 71 | 6 | 10 | 6 |
| 98 | 3 | 7 | 5 |

TABLE 2

| Nominal Thickness (microns) | Time to Reach 80% of Full Response (seconds, at 98% relative humidity) |
| --- | --- |
| 40 | 10 |
| 600 | 108 |

TABLE 3

Figure 1:
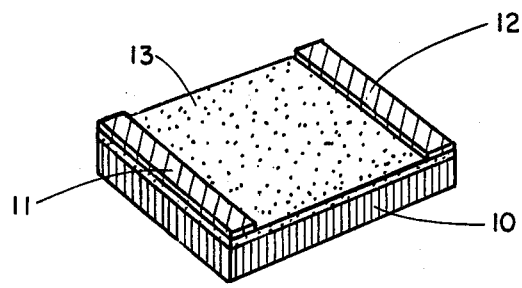
Figure 2:
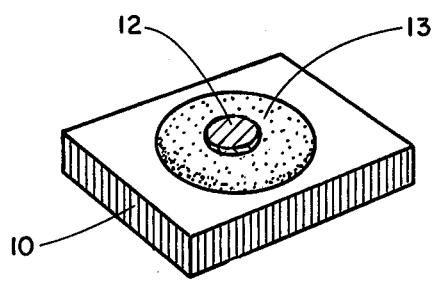
FIG. 2A is a perspective view of a further embodiment of the humidity sensitive resistor device in accordance with the present invention and FIG. 2B is a cross-sectional view of the device of FIG. 2A.
Figure 2A:
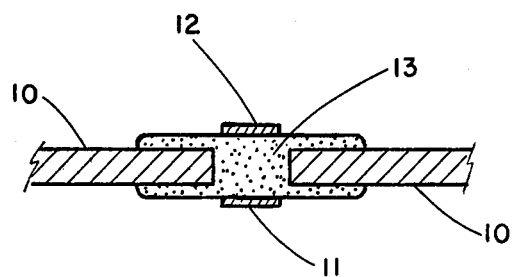
Figure 4:
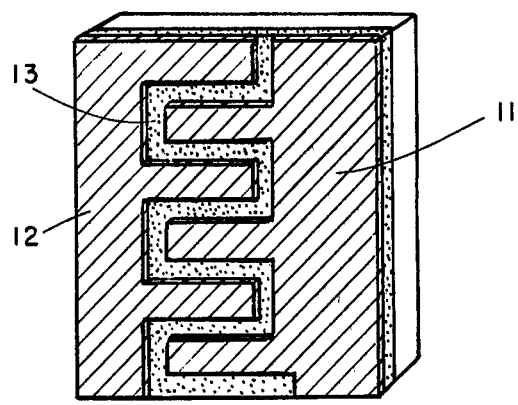
FIG. 4 is a perspective view of a further embodiment of the humidity sensitive resistor device in accordance with the present invention.

| | Humidity Sensor Configuration[1] | |
| --- | --- | --- |
| Relative Humidity (%) | Embodiment FIG. 1 Resistance, MΩ | Embodiment FIG. 4 |
| 31 | $10^3$ | 47.5 |
| 52 | 8.1 | 2.5 |
| 71 | 6.4 | 0.3 |
| 98 | 3.4 | 0.2 |

[1] nominal thickness of oxide layer 40 microns

TABLE 4

| Relative Humidity (%) | Nitrates Resistance (MΩ) | Chlorides |
| --- | --- | --- |
| 31 | 47.5 | 52.3 |
| 52 | 2.4 | 3.8 |
| 71 | .3 | .8 |
| 98 | .2 | .5 |

[1] nominal thickness of oxide layer 40 microns

The amplifier the circuit diagram of which is shown in FIG. 5 can be used in conjunction with a humidity detector according to the invention, for example for a threshold sensitivity detector. It is constructed so as to ignite an electric filament lamp or a signaling glowlamp 20 when moisture is formed on the detection area of the humidity detector symbolically represented by a resistor 21. In the said amplifier the resistor 21 is connected in series with a fixed resistor 22 between between the terminals of a supply source 23. The resistor 21 is connected to the positive terminal and the resistor 22 to the negative terminal. The base of an npn transistor 24 is connected to the junction point 25 of the resistors 21 and 22. The emitter of the transistor 24 is connected to the slider of a potentiometer 26 also connected between the terminals of the source 23. The collector of the transistor 24 is directly connected to the base of a pnp transistor 27 the emitter of which is connected to the positive terminal of the source 23, while the collector is connected to the base of an npn transistor 28 via a resistor 29. A resistor 30 may be included between the base of the transistor 28 and the negative terminal of the source 23 and serves as a leak resistor. The emitter of the transistor 28 is connected to the negative terminal of the source 23 and its collector is connected to a terminal of the lamp 20 the other terminal of which is connected to the positive terminal of the source 23.

The said amplifier is of a conventional type with continuous coupling between the various stages and hence its operation need not be described in more detail.

It should be mentioned that the emitter bias of the transistor 24 is adjusted by means of the potentiometer 26 in a manner such that the transistor 24 is cut off at the inoperative value of the resistor 21 (i.e., in the absence of moisture on the probe represented by this resistor 21). Because the transistor 24 is cut off, the transistors 27 and 28 are also cut off; as a result the lamp 22 is extinguished.

When the value of the resistor 21 is reduced by condensation of moisture, the potential of the junction point 25 becomes more positive so that the transistor 24 becomes conducting. The transistors 27 and 28 are successively rendered conductive and as a result a current traverses the lamp 22 which consequently emits light.

An amplifier for a detector of the type described may comprise the following components:
Transistors 24 and 28: BC 109
Transistor 27: BC 179
Resistance 21 of the humidity detector: 5 to 10 megohms in the inoperative condition and less than 1 megohm in the presence of mist
Resistor 22: about 4 megohms
Potentiometer 26:
  overall resistance 20 kilo-ohms,
  resistor 29—3 kilo-ohms and
  resistor 30—150 kilo-ohms
Lamp 20: current strength 50 mA.
Voltage supplied by the source 23: 4 to 4.5 volts The above described amplifier does not mean a limitation of the invention. Nevertheless such a circuit is interesting because of the fact that in the inoperative condition its consumption is very small (restricted to the consumption of the potentiometer 26) and particularly because of the fact that substantially no current flows in the resistor 21 of the probe, so that the temperature of this probe is not raised by remains equal to the temperature of the ambient atmosphere in which it is required to perform its monitoring function.

By means of a probe the mean resistance of which is about $10^6$ ohms in the inoperative condition and about $10^3$ ohms in the presence of moisture, the electric circuit of the detector can be greatly simplified and limited to connecting the probe in series with a signalling glowlamp and a suitable charge resistor, the assembly being fed by a low voltage source which may supply a direct current or an alternating current. Manufacture of such a detector is particularly economical.

What is claimed is:

1. A humidity sensitive semiconductor device comprising an insulating base member; and
  a humidity sensitive coating on said base member having at least two spread apart metal electrodes connected thereto, said coating consisting essentially of (a) a compound of the formula $L_{1-x}Sr_xCoO_3$ where L is a member of the lanthanide series of elements selected from the group consisting essentially of lanthanum, cerium, praseodymium, neodymium, promethium, samarium, europium, gadolinium, terbium, dysprosium, holmium, erbium, thulium, ytterbium, and lutetium and x is from near zero up to 0.5 and (b) an anion selected from the group consisting essentially of the organic anions of monobasic acids, dibasic acids or polybasic acids, inorganic anions and mixtures thereof.

2. The humidity sensitive semiconductor device in accordance with claim 1 wherein L is selected from the group consisting essentially of lanthanum, cerium, gadolinium, neodymium, praseodymium samarium and ytterbium.

3. The device in accordance with claim 2 wherein L is lanthanum.

4. The humidity sensitive semiconductor device in accordance with claim 1 wherein said humidity sensitive coating has a thickness of from about 10 microns to about 500 microns.

5. The humidity sensitive semiconductor device in accordance with claim 1 wherein said anion is present in the amount 0.05-5%.

* * * * *